United States Patent [19]

Matsuishi et al.

[11] Patent Number: 4,798,832
[45] Date of Patent: Jan. 17, 1989

[54] PYRIDO[1,2-A]PYRIMIDINE COMPOUNDS, CORRESPONDING INTERMEDIATES AND USE AS SRS-A ANTAGONISTS

[75] Inventors: Naoto Matsuishi, Kawaguchi; Yoshio Nakagawa, Kasukabe; Michiaki Amano, Koganei; Norihiko Kakehi, Yokohama; Toshio Kawashima, Washimiya; Shigeki Omura, Tokyo, all of Japan

[73] Assignee: Tokyo Tanabe Company, Limited, Japan

[21] Appl. No.: 37,786

[22] Filed: Apr. 13, 1987

[30] Foreign Application Priority Data

Apr. 16, 1986 [JP] Japan .................................. 61-86034

[51] Int. Cl.$^4$ .................. C07D 471/04; A61K 31/505
[52] U.S. Cl. ..................................... 514/258; 544/282; 546/312
[58] Field of Search .................... 544/282; 514/258

[56] References Cited

U.S. PATENT DOCUMENTS

| | | | |
|---|---|---|---|
| 4,122,274 | 10/1978 | Juby | 544/249 |
| 4,213,903 | 7/1980 | Bantick | 548/250 |
| 4,617,407 | 10/1986 | Young | 548/254 |
| 4,661,505 | 4/1987 | Marshall | 548/251 |
| 4,667,055 | 5/1987 | Gillard | 514/861 |

OTHER PUBLICATIONS

Morrison & Boyd, "Organic Chemistry", 2nd Ed., Allyn and Bacon, Inc., Boston (1966), pp. 562–565.

Primary Examiner—Donald G. Daus
Assistant Examiner—E. Bernhardt
Attorney, Agent, or Firm—McGlew and Tuttle

[57] ABSTRACT

Pyrido[1,2-a]pyrimidine derivatives of the general formula [I] and their physiologically acceptable salts are provided:

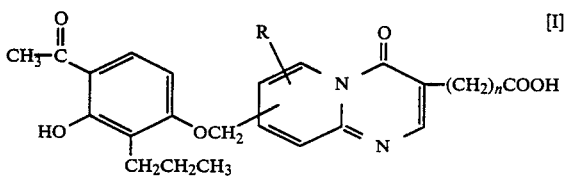

where R is a hydrogen atom, a halogen atom or a methyl group, and n is 0, 1 or 2. The pyrido[1,2-a]pyrimidine derivatives and their salts exhibit an excellent antagonistic effect on slow-reacting substance of anaphylaxis and, therefore, are useable for the treatment of allergic diseases.

45 Claims, No Drawings

PYRIDO[1,2-A]PYRIMIDINE COMPOUNDS, CORRESPONDING INTERMEDIATES AND USE AS SRS-A ANTAGONISTS

BACKGROUND OF THE INVENTION (1) Field of the Invention

This invention relates to pyrido[1,2-a]pyrimidine derivatives and physiologically acceptable salts thereof, which have a marked antagonistic effect on slow-reacting substance of anaphylaxis (hereinafter abbreviated as SRS-A) and, therefore, are useful for the treatment of Type I allergic diseases induced by SRS-A.

(2) Description of the Prior Art

SRS-A is strongly effective in causing contraction of smooth muscle and constitutes a substance responsible for Type I allergic diseases, particularly bronchial asthma and allergic rhinitis [Quarterly Journal of Experimental Physiology, Vol. 30, p. 121, 1940]. Leukotriene $D_4$ has been found to be a representative active component of this substance and the presence of an inhibitory effect on the in vivo activity of leukotriene $D_4$ is now considered to be a criterion of the usefulness of drugs for the treatment of Type I allergic diseases induced by SRS-A [Nature, Vol. 288, p. 484, 1980].

Drugs useful for the treatment of Type I allergic diseases induced by SRS-A are roughly divided into two types: drugs of the SRS-A release suppression type which act to prevent the release of SRS-A from mast cells or basophils and thereby inhibit its activity indirectly, and drugs of the SRS-A antagonistic type which act to antagonize the released SRS-A in the living body and thereby inhibit its activity directly. However, drugs of the SRS-A release suppression type are basically used for the purpose of preventing the induction of allergic attacks by SRS-A and generally tend to lack in effectiveness immediately after the onset of an attack. That is, they often fail to exhibit the so-called rapid-acting property. In recent years, therefore, it has been eagerly desired from the viewpoint of an immediate effect on allergic attacks to develop a satisfactorily effective drug of the SRS-A antagonistic type.

9-Benzyloxy-4-oxo-pyrido[1,2-a]pyrimidine-3-carboxylic acid (hereinafter abbreviated as Compound A) is a conventionally known pyridopyrimidine compound and it has been reported that this compound is useful as a central nervous system depressant (Japanese Patent Laid-Open No. 14495/'74, corresponding to U.S. Pat. No. 3,966,847).

SUMMARY OF THE INVENTION

In the above report, however, no suggestion is found of the effect that Compound A has a therapeutic effect on diseases related to allergy. In fact, a confirmatory experiment conducted by the present inventors has demonstrated that Compound A has no antagonistic effect on SRS-A as represented by leukotriene $D_4$. Accordingly, the present inventors have made an exhaustive study in the search for compounds antagonizing the in vivo activity of SRS-A and, in particular, leukotriene $D_4$. As a result, a novel compound having a marked antagonistic effect on leukotriene $D_4$ has been discovered among compounds analogous to Compound A. The present invention has been completed on the basis of this discovery.

According to one feature of the present invention, there are provided pyrido[1,2-a]pyrimidine derivatives of the general formula

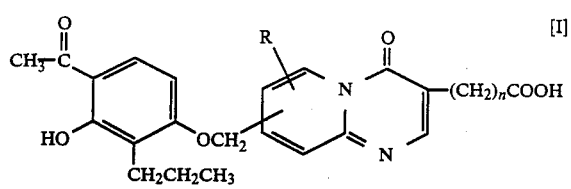

where R is a hydrogen atom, a halogen atom or a methyl group, and n is 0, 1 or 2, and physiologically acceptable salts thereof.

According to another feature of the present invention, there are provided processes for preparing pyrido[1,2-a]pyrimidine derivatives of the above general formula [I] and physiologically acceptable salts thereof.

According to still another feature of the prevent invention, there are provided pharmaceutical compositions useful for the treatment of allergic diseases containing, as an active ingredient, a pyrido[1,2-a]pyrimidine derivative of the above general formula [I] or a physiologically acceptable salt thereof. The pyrido[1,2-a]pyrimidine derivatives of the above general formula [I] and physiologically acceptable salts thereof will hereinafter be referred to generically as the present compounds [I].

DETAILED DESCRIPTION OF THE PREFERRED EMBODIMENTS

The present compound [I] can be prepared by hydrolyzing an ester derivative of the general formula

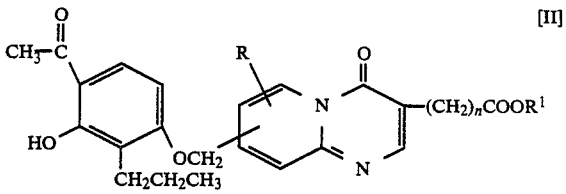

where R and n are as previously defined, and $R^1$ is a lower alkyl group, with an excess of an acid or an alkali.

Acids useful for this purpose include inorganic acids such as sulfuric acid, hydrochloric acid, etc. Useful alkalies include alkali metal hydroxides such as sodium hydroxide, potassium hydroxide, etc., and alkali metal carbonates such as sodium carbonate, potassium carbonate, etc. The hydrolysis is carried out in a water-containing organic solvent at a temperature of 0° to 150° C., preferably 20° to 100° C., for a period of time ranging from 1 minute to 72 hours.

Organic solvents suitable for use in the hydrolysis include lower alcohols such as methanol, ethanol, etc.; organic acids such as acetic acid, formic acid, etc.; and ethers such as tetrahydrofuran, dioxane, etc.

Physiologically acceptable salts of the pyrido[1,2-a]pyrimidine derivatives represented by the above general formula [I] can be prepared by reacting the corresponding pyrido[1,2-a]pyrimidine derivative wth an alkali metal or alkaline earth metal hydroxide (such as sodium hydroxide, potassium hydroxide, calcium hydroxide or the like), an alkali metal or alkaline earth metal carbonate (such as sodium carbonate, potassium carbonate, calcium carbonate or the like), an organic amine (such as ethanolamine, methylephedrine or the like) or ammonia in water, a lower alcohol or a mixture thereof. Lower alcohols useful for this purpose include methanol, ethanol, isopropanol, n-butyl alcohol and the like.

The ester derivatives represented by the above general formula [II] can be prepared by condensing 1 mole of a compound of the general formula

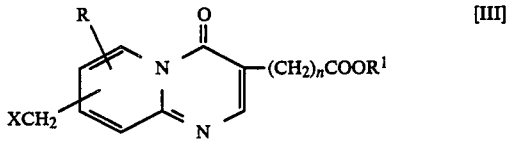
[III]

where R, $R^1$ and n are as previously defined and X is a chlorine or bromine atom, with 1 to 6 moles of 2,4-dihydroxy-3-n-propylacetohenone in the presence of an acid acceptor.

Acid acceptors useful for this purpose include alkali metal carbonates such as sodium carbonate, potassium carbonate, etc., and alkali metal hydroxides such as sodium hydroxide, potassium hydroxide, etc. In the reaction system, potassium iodide may also be present as a reaction accelerator.

Suitable reaction solvents include acetone, methyl ethyl ketone, diethyl ketone, cyclohexanone, dimethylformamide and dimethyl sulfoxide, as well as mixtures of two or more such solvents. The reaction is carried out by heating the reaction mixture at a temperature of 50° to 110° C. for a period of time ra-ging from 1 minute to 72 hours.

It has been confirmed by in vivo tests that the ester derivatives II prepared in the above-described manner also have practically as good an antagonistic effect on SRS-A as their corresponding carboxylic acids.

The compounds represented by the above general formula [III] can be prepared (1) by halogenating a compound of the general formula

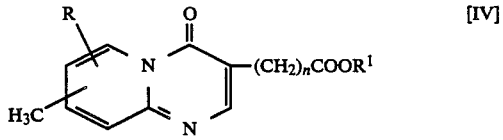
[IV]

where R, $R^1$ and n are as previously defined, with the aid of N-bromosuccinimide or N-chlorosuccinimide; (2) by halogenating a compound of the general formula

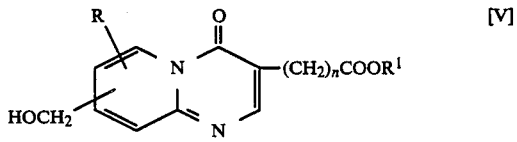
[V]

where R, $R^1$ and n are as previously defined, with the aid of a halogenating agent such as thionyl chloride, phosphoryl chloride, phosphoryl bromide, phosphorus trichloride, phosphorus tribromide or the like; of (3) by reacting a compound of the general formula

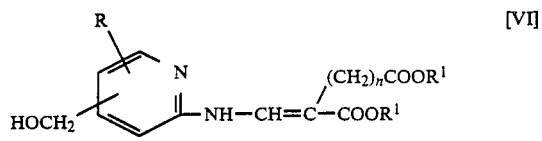
[VI]

where R, $R^1$ and n are as previously defined, with a mixture of phosphoryl chloride or phosphoryl bromide and polyphosphoric acid to effect its ring closure and halogenation at the same time.

The antagonistic effect on SRS-A of the present compounds [I] was tested according to the following experimental procedures using leukotriene $D_4$ which is a representative active component of SRS-A.

(i) In vitro tests

The antagonistic effect on leukotriene $D_4$ of the present compounds [I] was tested by using the terminal ileum excised from a male guinea pig of the Hartley strain. Specifically, the terminal ileum was suspended, under aerated conditions, in 10 ml of Tyrode's solution containing $5 \times 10^{-7}$M atropine and $1 \times 10^{-6}$M mepyramine. Then, a test compound and leukotriene $D_4$ (manufactured by Wako Junyaku Co., Ltd.) were successively added thereto with an interval of 30 seconds. After the lapse of 4 to 6 minutes, the degree of contraction of the ileum was measured with a Model TD-112S Isotonic Transducer (manufactured by Nippon Koden Co., Ltd.). The test compound and leukotriene $D_4$ were used in such amounts as to give concentrations of $10^{-9}$ to $10^{-3}$ g/ml and 0.3 ng/ml, respectively.

The antagonistic effect on leukotriene $D_4$ of each test compound was evaluated in terms of the concentration of the test compound at which the ileum contraction reaction induced by leukotriene $D_4$ was inhibited by 50% (hereinafter referred to as $IC_{50}$) Specifically, at varying concentrations of each test compound, the percent inhibition of contraction was calculated from the measured degree of contraction of the ileum according the following equation $$\text{Percent inhibition of contraction} = \frac{\text{(Degree of contraction without addition of test compound)} - \text{(Degree of contraction with addition of test compound)}}{\text{(Degree of contraction without addition of test compound)}} \times 100$$

On the basis of the data thus obtained, a dose-response curve was prepared and used to determine the $IC_{50}$ value of the test compound.

The test compounds used in these experiments were the compounds enumerated below and considered to be typical of the present compounds [I]. The designation given in parentheses after the chemical name of each compound means its tentative name as used herein and corresponds to the respective one of the examples which will be described later.

9-(4-Acetyl-3-hydroxy-2-n-propylphenoxymethyl)-4-oxo-pyrido[1,2-a]pyrimidine-3-carboxylic acid (Example 1).

[9-(4-Acetyl-3-hydroxy-2-n-propylphenoxymethyl)-4-oxo-pyrido[1,2-a]pyrimidin-3-yl]acetic acid (Example 2).

[9-(4-Acetyl-3-hydroxy-2-n-propylphenoxymethyl)-8-methyl-4-oxo-pyrido[1,2-a]pyrimidin-3-yl]acetic acid (Example 3).

3-[9-(4-Acetyl-3-hydroxy-2-n-propylphenoxymethyl)-4-oxo-pyrido[1,2-a]pyrimidin-3-yl]propionic acid (Example 4).

3-[9-(4-Acetyl-3-hydroxy-2-n-propylphenoxymethyl)-7-bromo-4-oxo-pyrido[1,2-a]pyrimidin-3-yl]propionic acid (Example 5).

3-[7-(4-Acetyl-3-hydroxy-2-n-propylphenoxymethyl)-4-oxo-pyrido[1,2-a]pyrimidin-3-yl propionic acid (Example 6).

3-[9-(4-Acetyl-3-hydroxy-2-n-propylphenoxymethyl)-4-oxo-pyrido[1,2-a]pyrimidin-3-yl]propionic acid potassium salt (Example 7).

The results thus obtained are shown in Table 1. For purposes of comparison, the antagonistic effect on leukotriene $D_4$ of Compound A was tested in the same manner as described above and the result is also shown in Table 1.

TABLE 1

| Test compound | Antagonistic effect on leukotriene $D_4$ $IC_{50}$ (µg/ml) |
| --- | --- |
| Compound A | 10.00 or greater |
| Example 1 | 0.03 |
| Example 2 | 0.04 |
| Example 3 | 0.80 |
| Example 4 | 0.01 |
| Example 5 | 0.30 |
| Example 6 | 0.40 |
| Example 7 | 0.03 |

(ii) In vivo tests

Using male guinea pigs of the Hartley strain, weighing about 400 g, in groups of six, the inhibitory effect of the present compounds [I] on the airway constriction reaction induced by leukotriene $D_4$ was tested according to the Konzett-Rössler procedure [Naunyn-Schmiederbergs Archiv för Experimentelle Pathologie und Pharmakologie, vol. 195, p. 71, 1904]. Specifically, each guinea pig was anesthetized by intraperitoneal administration of 1.5 g/kg of urethane and an incision was made in the neck to expose the trachea. To the exposed trachea was connected a respirator (with a ventilation volume of 5–7 ml, a respiration rate of 70 per minute, and a pulmonary load pressure of 10 cmH$_2$O; manufactured by Ugo Basile Biological Research Apparatus Co.) by way of a cannula. The volume of air overflowing through the branch of the cannula was measured by means of a Model 7020 Bronchospasm Transducer (manufactured by Ugo Basile Biological Research Apparatus Co.) and recorded with a Model RM-6000 Polygraph (manufactured by Nippon Koden Co., Ltd.).

The tests were carried out as follows: Each guinea pig was treated by intravenous injection of 1 mg/kg of gallamine triethiodide. Then, 5 mg/kg of a test compound and 0.5 µg/kg of leukotriene $D_4$ were successively administered thereto through the cervical vein with an interval of 2 minutes, and the volume of air overflowing as a result of the induced airway constriction reaction was measured. The test compound was used in the form of a solution in physiological saline containing sodium hydrogen carbonate, while leukotriene $D_4$ was used in the form of a solution in physiological saline.

In these experiments, the six compounds of Examples 1, 2, 4, 5, 6 and 7 were tested.

When each of these six compounds was used at a dose of 5 mg/kg, the airway constriction reaction induced by leukotriene $D_4$ was inhibited by 50% or greater. Thus, it can be seen that the present compounds [I] have a very excellent antagonistic effect on leukotriene $D_4$.

(iii) Toxicity test

The acute toxicity ($LD_{50}$) of several typical examples of the present compounds [I] was tested of 5-weeks-old male ddY strain mice and male SD straih rats. For this purpose, the compounds of Examples 2 and 4 were selected as typical examples. For mice, the $LD_{50}$ values of these two compounds were not less than 4.0 g/kg when administered orally, and not less than 100 mg/kg when administered intravenously. For rats, their $LD_{50}$ values were not less than 4.0 g/kg when administered orally, and not less than 200 mg/kg when administered intravenously.

On the basis of the results of the above-described in vitro, in vivo and toxicity tests, it may safely be said that the present compounds [I] are useful for the treatment of SRS-A induced Type I allergic diseases including, in particular, bronchial asthma and allergic rhinitis. The present compounds [I] may also be used as anti-ulcer agents, anti-inflammatory agents or drugs for the treatment of ischemic heart diseases.

In addition, it has also be confirmed by animal experiments using rats that the present compounds [I] has a marked protective effect on the liver.

The present compounds [I] may be admixed with physiologically inert solid or liquid pharmaceutical carriers to form pharmaceutical compositions. These compositions may have a variety of dosage forms including injectable solutions, tablets, capsules, powders, fine granules, granules, liquors, suspensions and emulsions. The pharmaceutical carriers can be any of various pharmaceutical carriers usually used in such dosage forms, and examples thereof include excipients, binders and disintegrants, such as corn starch, dextrin, α-, β- or γ-cyclodextrin, glucose, lactose, sucrose, methylcellulose, calcium carboxymethylcellulose, crystalline cellulose, magnesium stearate, sodium alginate, Witepsol W35, Witepsol E85, polyvinyl alcohol, light silicic acid anhydride, etc.; lubricants such as talc, stearic acid, waxes, hydroxypropylcellulose, boric acid, etc.; coating agents such as shellac, cellulose acetate phthalate, polyvinyl acetal diethylaminoacetate, etc.; solubilizing agents such as glycerol, propylene glycol, mannitol, etc.; emulsifying or suspending agents such as polyoxyethylene stearate, polyoxyethylene cetyl alcohol ether, gum arabic, polyvinylpyrrolidone, etc.; stabilizers such as sorbitol, Tween 80, Span 60, fats and oils, etc.; and various solvents.

In the above-described pharmaceutical compositions, the present compound [I] should be contained in such an amount that the daily dose of the active ingredient is in the range of 0.002 to 60 mg/kg, preferably 0.02 to 10 mg/kg, for purposes of oral administration or in the range of 1 to 1000 µg/kg, preferably 10 to 200 µkg, for purposes of intravenous injection.

The present invention is further illustrated by the following Reference Examples, Examples and Pharmaceutical Compositions.

Reference Examples (Preparation of Ester Derivatives [II])

2.40 g (7.38 mmoles) of [9-bromomethyl-4-oxo-pyrido[1,2-a]pyrimidin-3-yl]acetic acid ethyl ester, 1.45 g (7.47 mmoles) of 2,4-dihydroxy-3-n-propylacetophenone and 1.50 g of anhydrous potassium carbonate were added to 200 ml of methyl ethyl ketone, and this mixture was heated under reflux for 2 hours with stirring. After cooling, the resulting reaction solution was filtered to remove any insoluble matter, the filtrate was evaporated under reduced pressure, and the residue thus obtained was purified by silica gel column chromatography. Fractions containing the desired compound were collected and evaporated to dryness under reduced pressure. The resulting residue was recrystallized from ethanol to obtain 2.30 g (70% yield) of [9-(4-acetyl-3-hydroxy-2-n-propylphenoxymethyl)-4-oxo-pyrido[1,2-a]pyrimidin-3-yl]acetic acid ethyl ester. This product had a melting point of 134°–135° C.

The thirteen compounds enumerated below were prepared in substantially the same manner as described above, except that the [9-bromomethyl-4-oxo-pyrido[1,2-a]pyrimidin-3-yl]acetic acid ethyl ester was replaced by each of the corresponding compounds [III] and that the molar ratio of reactants and the reaction conditions were suitably modified. Thus, these compounds were obtained in a yield ranging from 41% to 91%.

9-(4-Acetyl-3-hydroxy-2-n-propylphenoxymethyl)-4-oxo-pyrido[1,2-a]pyrimidine-3-carboxylic acid ethyl ester [M.P. 165°–171° C (on recrystallization from methyl ethyl ketone)].

[9-(4-Acetyl-3-hydroxy-2-n-propylphenoxymethyl)-8-methyl-4-oxo-pyrido[1,2-a]pyrimidin-3-yl]acetic acid ethyl ester [M.P. 144°–145° C. (on recrystallization from ethanol)].

3-[9-(4-Acetyl-3-hydroxy-2-n-propylphenoxymethyl)-4-oxo-pyrido[1,2-a]pyrimidin-3-yl]propionic acid ethyl ester [M.P. 116°–118° C. (on recrystallization from ethanol)].

3-[9-(4-Acetyl-3-hydroxy-2-n-propylphenoxymethyl)-7-bromo-4-oxo-pyrido[1,2-a]pyrimidin-3-yl]propionic acid ethyl ester [M.P. 153°–155° C. (on recrystallization from methyl ethyl ketone)].

3-[7-(4-Acetyl-3-hydroxy-2-n-propylphenoxymethyl)-4-oxo-pyrido[1,2-a]pyrimidin-3-yl]propionic acid ethyl ester [M.P. 157°–159° C. (on recrystallization from ethanol)].

8-(4-Acetyl-3-hydroxy-2-n-propylphenoxymethyl)-4-oxo-pyrido[1,2-a]pyrimidine-3-carboxylic acid ethyl ester.

9-(4-Acetyl-3-hydroxy-2-n-propylphenoxymethyl)-6-fluoro-4-oxo-pyrido[1,2-a]pyrimidine-3-carboxylic acid ethyl ester.

9-(4-Acetyl-3-hydroxy-2-n-propylphenoxymethyl)-7-methyl-4-oxo-pyrido[1,2-a]pyrimidine-3-carboxylic acid ethyl ester.

9-(4-Acetyl-3-hydroxy-2-n-propylphenoxymethyl)-4-oxo-pyrido[1,2-a]pyrimidine-3-carboxylic acid isopropyl ester.

[7-(4-Acetyl-3-hydroxy-2-n-propylphenoxymethyl)-4-oxo-pyrido[1,2-a]pyrimidin-3-yl]acetic acid ethyl ester.

[7-(4-Acetyl-3-hydroxy-2-n-propylphenoxymethyl)-8-chloro-4-oxo-pyrido[1,2-a]pyrimidin-3-yl]acetic acid ethyl ester.

[9-(4-Acetyl-3-hydroxy-2-n-propylphenoxymethyl)-4-oxo-pyrido[1,2-a]pyrimidin-3-yl]acetic acid n-butyl ester.

3-[9-(4-Acetyl-3-hydroxy-2-n-propylphenoxymethyl)-4-oxo-pyrido[1,2-a]pyrimidin-3-yl]propionic acid methyl ester.

EXAMPLE 1

0.90 g (2.12 mmoles) of 9-(4-acetyl-3-hydroxy-2-n-propylphenoxymethyl)-4-oxo-pyrido[1,2-a]pyrimidine-3carboxylic acid ethyl ester and 8 ml of 6N hydrochloric acid were added to 36 ml of acetic acid, and this mixture was heated at 80° C. for 8 hours with stirring. After cooling, the resulting reaction solution was concentrated under reduced pressure, followed by the addition of an appropriate amount of water. The solid matter which separated out was collected by filtration and washed with water. This precipitate was dried and then recrystallized from a mixture of tetrahydrofuran and methanol to obtain 0.42 g (50% yield) of 9-(4-acetyl-3-hydroxy-2-n-propylphenoxymethyl)-4-oxo-pyrido[1,2-a]-pyrimidine-3-carboxylic acid in the form of white crystals. These crystals had a melting point of 170°–172° C.

Infrared absorption spectrum (cm$^{-1}$, KBr): 1740, 1620, 1270.

Analysis:

Calcd. for $C_{21}H_{20}N_2O_6$ (%) C, 63.63; H, 5.09; N, 7.07. Found (%) C, 63.51; H, 5.13; N, 7.01.

EXAMPLE 2

0.81 g (1.85 mmoles) of [9-(4-acetyl-3-hydroxy-2-n-propylphenoxymethyl)-4-oxo-pyrido[1,2-a]pyrimidin-3-yl]acetic acid ethyl ester and 20 ml (5.00 mmoles) of a 1% aqueous solution of sodium hydroxide were mixed with and dissolved in 30 ml of ethanol, and this mixture was stirred at room temperature for 3 hours. The resulting reaction solution was diluted with an appropriate amount of water and then neutralized with dilute hydrochloric acid. The solid matter which separated out was collected by filtration, washed with water and then dried. This precipitate was recrystallized from acetonitrile to obtain 0.59 g (78% yield) of [9-(4-acetyl-3-hydroxy-2-n-propylphenoxymethyl)-4-oxo-pyrido[1,2-a]pyrimidin-3-yl]acetic acid in the form of white crystals. These crystals had a melting point of 239°–243° C.

Infrared absorption spectrum (cm$^{-1}$, KBr): 2600–2500, 1720, 1700, 1635, 1275.

Analysis: Calcd. for $C_{22}H_{22}N_2O_6$ (%) C, 64.38; H, 5.40; N, 6.83; Found (%) C, 64.36; H, 5.49; N, 6.78.

The compounds of the following Examples 3–6 were prepared in substantially the same manner as described in Example 2 above, except that the [9-(4-acetyl-3-hydroxy-2-n-propylphenoxymethyl)-4-oxo-pyrido[1,2-a]pyrimidin-3-yl]acetic acid ethyl ester (1.85 mmoles) was replaced by each of the corresponding ester derivatives [II] (1.85 mmoles).

EXAMPLE 3

There was obtained 0.42 g (54% yield) of [9-(4-acetyl-3-hydroxy-2-n-propylphenoxymethyl)-8-methyl-4-oxopyrido[1,2-a]pyrimidin-3-yl]acetic acid in the form of white crystals. On recrystallization from acetonitrile, these crystals had a melting point of 191°–193° C.

Infrared absorption spectrum (cm$^{-1}$, KBr): 2700–2500, 1730, 1675, 1635, 1275.

Analysis: Calcd. for $C_{23}H_{24}N_2O_6$ (%) C, 65.08; H, 5.70; N, 6.60; Found (%) C, 65.23; H, 5.57; N, 6.72.

EXAMPLE 4

There was obtained 0.65 g (83% yield) of 3-[9-(4-acetyl-3-hydroxy-2-n-propylphenoxymethyl)-4-oxo-pyrido[1,2-a]pyrimidin-3-yl]propionic acid in the form of white crystals. On recrystallization from acetic acid, these crystals had a melting point of 210°–214° C.

Infrared absorption spectrum (cm$^{-1}$, KBr): 2700–2500, 1720, 1680, 1625, 1270.

Analysis: Calcd. for $C_{23}H_{24}N_2O_6$ (%) C, 65.08; H, 5.70; N, 6.60; Found (%) C, 65.01; H, 5.72; N, 6.48

EXAMPLE 5

There was obtained 0.49 g (53% yield) of 3-[9-(4-acetyl-3-hydroxy-2-n-propylphenoxymethyl)-7-bromo-4-oxopyrido[1,2-a]pyrimidin-3-yl]propionic acid in the form of pale-yellow crystals. On recrystallation from ethanol, these crystals had a melting point of 239°–242° C.

Infrared absorption spectrum (cm$^{-1}$, KBr): 2700–2500, 1715, 1695, 1630, 1270.

Analysis: Calcd. for $C_{23}H_{23}BrN_2O_6$ (%) C, 54.88; H, 4.61; N, 5.57 Found (%) C, 55.03; H, 4.50; N, 5.55

EXAMPLE 6

There was obtained 0.54 g (69% yield) of 3-[7-(4-acetyl-3-hydroxy-2-n-propylphenoxymethyl)-4-oxo-pyrido[1,2-a]pyrimidin-3-yl]propionic acid in the form of white crystals. On recrystallization from ethanol, these crystals had a melting point of 190°–194° C.

Infrared absorption spectrum (cm$^{-1}$, KBr): 2700–2500, 1720, 1680, 1625, 1270.

Analysis: Calcd. for $C_{23}H_{24}N_2O_6$ (%) C, 65.08; H, 5.70; N, 6.60; Found (%) C, 65.21; H, 5.65; N, 6.61.

EXAMPLE 7

0.50 g (1.18 mmoles) of 3-[9-(4-acetyl-3-hydroxy-2-n-propylphenoxymethyl)-4-oxo-pyrido[1,2-a]pyrimidin-3yl]propionic acid was suspended in 20 ml of ethanol, and 3.90 ml (1.18 mmoles) of a 2% ethanolic solution of potassium hydroxide was added thereto. This suspension was stirred until a clear solution was obtained. To the resulting reaction solution was added a small amount of n-hexane. The solid matter which separated out was collected by filtration and then dried to obtain 0.40 g (73% yield) of 3-[9-(4-acetyl-3-hydroxy-2-n-propyl-phenoxymethyl)-4-oxo-pyrido[1,2-a]pyrimidin-3-yl]propionic acid potassium salt in the form of white powder.

Infrared absorption spectrum (cm$^{-1}$, KBr) 1680, 1630, 1270.

Analysis: Calcd. for $C_{23}H_{23}KN_2O_6$ (%) C, 59.72; H, 5.01; N, 6.06; Found (%) C, 59.84; H, 5.08; N, 6.00

In addition, the three compounds enumerated below were prepared in substantially the same manner as described in Example 1.

8-(4-Acetyl-3-hydroxy-2-n-propylphenoxymethyl)-4-oxo-pyrido[1,2-a]pyrimidine-3-carboxylic acid.

9-(4-Acetyl-3-hydroxy-2-n-propylphenoxymethyl)-6-fluoro-4-oxo-pyrido[1,2-a]pyrimidine-3-carboxylic acid.

9-(4-Acetyl-3-hydroxy-2-n-propylphenoxymethyl)-7-methyl-4-oxo-pyrido[1,2-a]pyrimidine-3-carboxylic acid.

Furthermore, the two compounds enumerated below were prepared in substantially the same manner as described in Example 2.

[7-(4-Acetyl-3-hydroxy-2-n-propylphenoxymethyl)-4-oxo-pyrido[1,2-a]pyrimidin-3-yl]acetic acid.

[7-(4-Acetyl-3-hydroxy-2-n-propylphenoxymethyl)-8-chloro-4-oxo-pyrido[1,2-a]pyrimidin-3-yl]acetic acid.

| Pharmaceutical Composition 1 (tablets) | |
|---|---|
| | % by weight |
| (1) Compound of Example 2 | 10.0 |
| (2) Lactose | 56.0 |
| (3) Corn starch | 15.0 |
| (4) Crystalline cellulose | 15.0 |
| (5) Hydroxypropylcellulose | 3.0 |
| (6) Magnesium stearate | 1.0 |
| | 100.0 |

The above ingredients (1)–(5) were blended together. After the addition of water, the resulting mixture was granulated and then dried. The granules so formed were adjusted to a predetermined size range, and the ingredient (6) was added thereto. The resulting mixture was compressed to form tablets each containing 10 mg of the active ingredient.

| Pharmaceutical Composition 2 (capsules) | |
|---|---|
| | % by weight |
| (1) Compound of Example 4 | 10.0 |
| (2) Lactose | 65.5 |
| (3) Corn starch | 20.0 |
| (4) Hydroxypropylcellulose | 3.0 |
| (5) Light silicic acid anhydride | 0.5 |
| (6) Magnesium stearate | 1.0 |
| | 100.0 |

According to conventional procedure, the above ingredients were blended together and then granulated. The granules so formed were filled into capsules, each of which contained 10 mg of the active ingredient.

What is claimed is:

1. A pyrido[1,2-a]pyrimidine compound of the formula

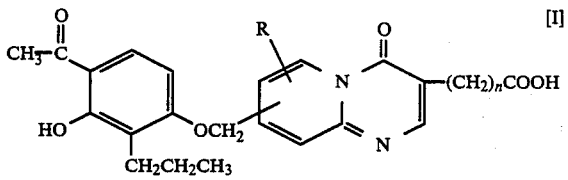

where R is a hydrogen atom, a halogen atom or methyl group, and n is 0, 1 or 2, or a physiologically acceptable salt thereof.

2. A compound as claimed in claim 1 where, in the pyrido[1,2-a]pyrimidine ring, the 4-acetyl-3-hydroxy-2-n-propylphenoxymethyl group is substituted at the 7 or 9 position when R is substituted at the 8 position, or at the 9 position when R is substituted at the 7 position.

3. A compound as claimed in claim 2 wherein R is a hydrogen atom, a bromine atom or a methyl group.

4. A compound as claimed in any one of claims 1 to 3 wherein the physiologically acceptable salt is a sodium salt, a potassium salt or calcium salt.

5. A compound as claimed in claim 1 wherein n is 0.

6. A compound as claimed in claim 5 which is 9-(4-acetyl-3-hydroxy-2-n-propylphenoxymethyl)-4-oxo-pyrido[1,2-a]pyrimidine-3-carboxylic acid.

7. A compound as claimed in claim 1 wherein n is 1.

8. A compound as claimed in claim 7 which is [9-(4-acetyl-3-hydroxy-2-n-propylphenoxymethyl)-4-oxo-pyrido[1,2-a]pyrimidin-3-yl]acetic acid.

9. A compound as claimed in claim 7 which is [9-(4-acetyl-3-hydroxy-2-n-propylphenoxymethyl)-8-methyl-4-oxopyrido[1,2-a]pyrimidin-3-yl]acetic acid.

10. A compound as claimed in claim 1 wherein n is 2.

11. A compound as claimed in claim 10 which is 3-[9-(4-acetyl-3-hydroxy-2-n-propylphenoxymethyl)-4-oxo-pyrido[1,2-a]pyrimidin-3-yl]propionic acid.

12. A compound as claimed in claim 10 which is 3-[9-(4-acetyl-3-hydroxy-2-N-propylphenoxymethyl)-7-bromo-4-oxo-pyrido[1,2-]pyrimidin-3-yl]propionic acid.

13. A compound as claimed in claim 10 which is 3-[7-(4-acetyl-3-hydroxy-2-n-propylphenoxymethyl)-4-oxopyrido[1,2-a]pyrimidin-3-yl]propionic acid.

14. A compound as claimed in claim 10 which is 3-[9-(4-acetyl-3-hydroxy-2-N-propylphenoxymethyl)-4-oxo-pyrido[1,2-a]pyrimidin-3-yl]propionic acid potassium salt.

15. An ester compound of the formula $$\text{[II]}$$

where R is a hydrogen atom, a halogen atom or a methyl group, $R^1$ is a lower alkyl group and n is 0, 1 or 2.

16. A compound as claimed in claim 15 where, in the pyrido[1,2-a]pyrimidine ring, the 4-acetyl-3-hydroxy-2-n-propylphenoxymethyl group is substituted at the 7 or 9 position when R is substituted at the 8 position, or at the 9 position when R is substituted at the, 7 position.

17. A compound as claimed in claim 16 wherein R is a hydrogen atom, a bromine atom or a methyl group.

18. A compound as claimed in any one of claims 15 to 17 wherein $R^1$ is a methyl group, an ethyl group, an isopropyl group or a n-butyl group.

19. A compound as claimed in claim 19 wherein n is 0.

20. A compound as claimed in claim 19 which is 9-(4-acetyl-3-hydroxy-2-n-propylphenoxymethyl)-4-oxo-pyrido[1,2-a]pyrimidine-3-carboxylic acid ethyl ester.

21. A compound as claimed in claim 19 which is 9-(4-acetyl-3-hydroxy-2-n-propylphenoxymethyl)-4-oxo-pyrido[1,2-a]pyrimidine-3-carboxylic acid isopropyl ester.

22. A compound as claimed in claim 15 wherein n is 1.

23. A compound as claimed in claim 22 which is [9(4-acetyl-3-hydroxy-2-n-propylphenoxymethyl)-4-oxo-pyrido[1,2-a]pyrimidin-3-yl]acetic acid ethyl ester.

24. A compound as claimed in claim 22 which is [9-(4-acetyl-3-hydroxy-2-n-propylphenoxymethyl)-8-methyl-4-oxo-pyrido[1,2-a]pyrimidin-3-yl]acetic acid ethyl ester.

25. A compound as claimed in claim 22 which is [9(4-acetyl-3-hydroxy-2-n-propylphenoxymethyl)-4-oxo-pyrido[1,2-a]pyrimidin-3-yl]acetic acid n-butyl ester.

26. A compound as claimed in claim 15 wherein n is 2.

27. A compound as claimed in claim 26 which is 3-[9(4-acetyl-3-hydroxy-2-n-propylphenoxymethyl)-4-oxo-pyrido[1,2-a]pyrimidin-3-yl]propionic acid ethyl ester.

28. A compound as claimed in claim 26 which is 3-[9-(4-acetyl-3-hydroxy-2-n-propylphenoxymethyl)-7-bromo-4-oxo-pyrido[1,2-a]pyrimidin-3-yl]propionic acid ethyl ester.

29. A compound as claimed in claim 26 which is 3-[7-(4-acetyl-3-hydroxy-2-n-propylphenoxymethyl)-4-oxo-pyrido[1,2-a]pyrimidin-3-yl]propionic acid, ethyl ester.

30. A compound as claimed in claim 26 which is 3-[9-(4-acetyl-3-hydroxy-2-n-propylphenoxymethyl)-4-oxo-pyrido[1,2-a]pyrimidin-3-yl]propionic acid methyl ester.

31. Pharmaceutical composition useful for the treatment of allergic diseases induced by SRS-A comprising a daily dose for purpose of oral administration ranging from 0.02 to 10 mg/kg of a compound of claim 1 and one or more physiologically inert pharmaceutical carriers.

32. Pharmaceutical composition useful for the treatment of allergic diseases induced by SRS-A comprising a daily dose for purpose of intravenous injection ranging from 10 to 200 μg/kg of a compound of claim 1 and one or more physiologically inert pharmaceutical carriers.

33. Pharmaceutical composition useful for the treatment of allergic diseases induced by SRS-A comprising a therapeutically effective amount of a compound of claim 1 or 15 and a pharmaceutical carrier therefor.

34. A pharmaceutical composition as claimed in any one of claims 31 to 33 wherein the pyrido[1,2-a]pyrimidine compound is 9-(4-acetyl-3-hydroxy-2-n-propylphenoxymethyl)-4-oxo-pyrido[1,2-a]pyrimidine-3carboxylic acid.

35. A pharmaceutical composition as claimed in any one of claims 31 to 33 wherein the pyrido[1,2-a]pyrimidine compound is [9-(4-acetyl-3-hydroxy-2-n-propylphenoxymethyl)-4-oxo-pyrido[1,2-a]pyrimidin-3-yl]acetic acid.

36. A pharmaceutical composition as claimed in any one of claims 31 to 33 wherein the pyrido[1,2-a]pyrimidine derivative is 3-[9-(4-acetyl-3-hydroxy-2-n-propylphenoxymethyl)-4-oxo-pyrido[1,2-a]pyrimidin-3-yl]propionic acid.

37. A pharmaceutical composition as claimed in any one of claims 31 ro 33 wherein the pyrido[1,2-a]-pyrimidine compound is 3-[9-(4-acetyl-3-hydroxy-2-n-propylphenoxymethyl)-7-bromo-4-oxo-pyrido[1,2-a]pyrimidin-3-yl,]propionic acid.

38. A pharmaceutical composition as claimed in any one of claims 31 to 33 wherein the pyrido[1,2-a]pyrimidine compound is 3-[7-(4-acetyl-3-hydroxy-2-n-propylphenoxymethyl)-4-oxo-pyrido[1,2-a]pyrimidin-3-yl]-propionic acid.

39. A pharmaceutical composition as claimed in any one of claims 31 to 33 wherein the pyrido[1,2-a]pyrimidine compound is 3-[9-(4-acetyl-3-hydroxy-2-n-propylphenoxymethyl)-4-oxo-pyrido[1,2-a]pyrimidin-3-yl]propionic acid potassium salt.

40. Method of using a compound of claim 1 for the treatment of allergic diseases induced by grs-A comprising orally or intravenously administering a therapeutically effective amount of such compound of claim 1 to a patient.

41. Method of using a compound of claim 1 for the treatment of allergic diseases wherein the allergic disease is bronchial asthma or allergic rhinitis comprising orally or intravenously administering a therapeutically effective amount of such compound of claim 1 to a patient.

42. Method of using a compound of claim 15 for the treatment of allergic disease induced by SRS-A comprising orally or intravenously administering a therapeutically effective amount of such compound of claim 15 to a patient.

43. Method of using a compound of claim 15 for the treatment of allergic diseases wherein the allergic disease is bronchial asthma or allergic rhinitis comprising orally or intravenously administering a therapeutically effective amount of such compound of claim 15 to a patient 44. A method for treating allergic diseases induced by SRS-A comprising orally or intravenously administering a corresponding pharmaceutical composition of claim 31 or 32 to a patient.

45. A method claimed in claim 44 wherein the allergic disease is bronchial asthma or allergic rhinitis.

* * * * *